United States Patent
Fowler et al.

(10) Patent No.: US 11,135,145 B2
(45) Date of Patent: Oct. 5, 2021

(54) HESPERETIN AND TRANS-RESVERATROL COMPOSITIONS AND METHODS THEREOF

(71) Applicants: Paul John Thornalley, Kenilworth (GB); Naila Rabbani, Kenilworth (GB); Mingzhan Xue, Colchester (GB)

(72) Inventors: Mark Ian Fowler, Bedfordshire (GB); Gail Jenkins, Bedfordshire (GB); David James Messenger, Bedfordshire (GB); Naila Rabbani, Coventry (GB); Paul John Thornalley, Coventry (GB); Mingzhan Xue, Coventry (GB)

(73) Assignees: Paul John Thornally, Coventry (GB); Naila Rabbani, Coventry (GB); Mingzhan Xue, Coventry (GB)

( * ) Notice: Subject to any disclaimer, the term of this patent is extended or adjusted under 35 U.S.C. 154(b) by 0 days.

(21) Appl. No.: 15/775,692

(22) PCT Filed: Nov. 7, 2016

(86) PCT No.: PCT/EP2016/076858
§ 371 (c)(1),
(2) Date: May 11, 2018

(87) PCT Pub. No.: WO2017/080958
PCT Pub. Date: May 18, 2017

(65) Prior Publication Data
US 2018/0344603 A1 Dec. 6, 2018

(30) Foreign Application Priority Data
Nov. 13, 2015 (EP) .................................. 15194461.8

(51) Int. Cl.
| | |
|---|---|
| *A61K 31/35* | (2006.01) |
| *A61K 8/49* | (2006.01) |
| *A61K 8/34* | (2006.01) |
| *A61Q 7/00* | (2006.01) |
| *A61P 9/00* | (2006.01) |
| *A61K 31/05* | (2006.01) |

(Continued)

(52) U.S. Cl.
CPC .............. *A61K 8/498* (2013.01); *A61K 8/347* (2013.01); *A61K 31/05* (2013.01); *A61K 31/09* (2013.01); *A61K 31/353* (2013.01); *A61P 9/00* (2018.01); *A61Q 7/00* (2013.01)

(58) Field of Classification Search
CPC ........ A61K 8/498; A61K 31/05; A61K 8/347; A61K 31/353; A61Q 7/00
See application file for complete search history.

(56) References Cited

U.S. PATENT DOCUMENTS

| | | |
|---|---|---|
| 2007/0129428 A1 | 6/2007 | Richelle et al. |
| 2009/0082473 A1 | 3/2009 | De La Torre et al. |

FOREIGN PATENT DOCUMENTS

| | | |
|---|---|---|
| CN | 103462944 A | 12/2013 |
| EP | 0 920 870 A1 | 6/1999 |

(Continued)

OTHER PUBLICATIONS

Arck, P.C., et al., "Towards a 'Free Radical Theory of Graying': Melanocyte Apoptosis in the Aging Human Hair Follicle Is an Indicator of Oxidative Stress Induced Tissue Damage," FASEB Journal 2:1567-1569, Jul. 2006.

(Continued)

*Primary Examiner* — Shobha Kantamneni
(74) *Attorney, Agent, or Firm* — Christensen O'Connor Johnson Kindness PLLC

(57) ABSTRACT

The invention relates to a composition, in particular to an oral anti-ageing composition for treating hair ageing. This invention is based on the observation that the combination of hesperetin, a flavanone, derivable from a natural rutinoside hesperetin 7-rutinoside (also known as hesperidin) in *citrus*, e.g., in *Citrus aurantium* L, *Citrus sinensis*, *Zanthozylum gilletti*, leaves of *Agathosma serratifolia*, and trans-resveratrol synergistically up-regulates NQO-1 in a gene expression assay. The combination also induces Glo1, decreases MG and MG-protein glycation, decreases insulin resistance, decreases fasting plasma glucose, induces modest weight loss, improves renal function, decreases vascular inflammation marker sICAM-1, improves arterial dilatation and decreases the risk of cardiovascular disease. Thus is one aspect of the invention, a composition is provided, the composition comprising a combination of: (a) 30-10000, preferably 60-5000, most preferably 60-2500 mg in the form of an equivalent daily dose of flavanone of structure (I) wherein R is —H or —CH3, and mono-, di- and tri-acylated derivatives thereof; and (b) 20-1000, preferably 45-750, most preferably 45-500 mg in the form of an equivalent daily dose stilbenoid, wherein the composition comprises at least 0.5% w/w flavanone of structure I.

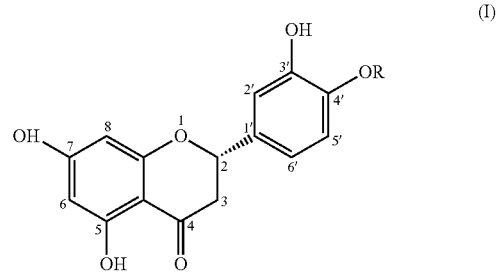

13 Claims, No Drawings

(51) Int. Cl.
   *A61K 31/09*  (2006.01)
   *A61K 31/353* (2006.01)

(56) References Cited

FOREIGN PATENT DOCUMENTS

| WO | 2014/095289 A2 | | 6/2014 |
|---|---|---|---|
| WO | WO2014086632 | * | 6/2014 |
| WO | 2015/171598 A1 | | 11/2015 |

OTHER PUBLICATIONS

Boocock, D.J., et al., "Phase I Dose Escalation Pharmacokinetic Study in Healthy Volunteers of Resveratrol, a Potential Cancer Chemopreventive Agent," Cancer Epidemiology Biomarkers & Prevention 16(6):1246-1252, Jun. 2007.
Cullinan, S.B., et al., "The Keap1-BTB Protein Is an Adaptor That Bridges Nrf2 to a Cul3-Based E3 Ligase: Oxidative Stress Sensing by a Cul3-Keap1 Ligase," Molecular and Cellular Biology 24(19):8477-8486, Oct. 2004.
Foerster, A., and T. Henle, "Glycation in Food and Metabolic Transit of Dietary AGEs (Advanced Glycation End-Products): Studies on the Urinary Excretion of Pyrraline," Biochemical Society Transactions 31:1383-1385, Dec. 2003.
Hybertson, B.M., et al., "Oxidative Stress in Health and Disease: The Therapeutic Potential of Nrf2 Activation," Molecular Aspects of Medicine 32(4-6):234-246, Aug.-Dec. 2011.
Itoh, K., et al., "An Nrf2/Small Maf Heterodimer Mediates the Induction of Phase II Detoxifying Enzyme Genes Through Antioxidant Response Elements," Biochemical and Biophysical Research Communications 236(2):313-322, Jul. 1997.
Kobayashi, A., et al., "Oxidative Stress Sensor Keap1 Functions as an Adaptor for Cul3-Based E3 Ligase to Regulate Proteasomal Degradation of Nrf2," Molecular and Cellular Biology 24(16):7130-7139, Aug. 2004.
Larance, M., and A.I. Lamond, "Multidimensional Proteomics for Cell Biology," Nature Reviews: Molecular Cell Biology 12(5):638-650, May 2015.
Lee, J.-M., and J.A. Johnson, "An Important Role of Nrf2-Are Pathway in the Cellular Defense Mechanism," Biochemistry and Molecular Biology 37(2):139-143, Mar. 2004.
Lu, Z., et al., "Profiling the Response of Human Hair Follicles to Ultraviolet Radiation," Journal of Investigative Dermatology 129(7):1790-1801, Jul. 2009.
Malhotra, D., et al., "Global Mapping of Binding Sites for Nrf2 Identifies Novel Targets in Cell Survival Response Through ChIP-Seq Profiling and Network Analysis," Nucleic Acids Research 38(17):5718-5734, 2010.
Moi, P., et al., "Isolation of NF-E2-Related Factor 2 (Nrf2), a NF-E2-Like Basic Leucine Zipper Transcriptional Activator That Binds to the Tandem NF-E2/AP1 Repeat of the f-globin locus Control Region," Proceedings of the National Academy of Sciences of the USA (PNAS) 91:9926-9930, Oct. 1994.
Parhiz, H., et al., "Antioxidant and Anti-Inflammatory Properties of the Citrus Flavonoids Hesperidin and Hesperetin: An Updated Review of Their Molecular Mechanisms and Experimental Models," Phytotherapy Research 29(3):323-331, Mar. 2015.
Rabbani, N., and P.J. Thornalley, "Dicarbonyl Stress in Cell and Tissue Dysfunction Contributing to Ageing and Disease," Biochemical and Biophysical Research Communications 458(2):221-226, Mar. 2015.
Sekhar, K.R., et al., "Cysteine-Based Regulation of the CUL3 Adaptor Protein Keap1," Toxicology and Applied Pharmacology 244(1):21-26, Apr. 2010. (Author Manuscript provided, PMCID: PMC2837771, available in PMC Apr. 1, 2011, 12 pages.).
Thornalley, P.J., et al., "Quantitative Screening of Advanced Glycation Endproducts in Cellular and Extracellular Proteins by Tandem Mass Spectrometry," Biochemical Journal 375(Pt 3):581-592, Nov. 2003.
Vang, O., et al., "What Is New for an Old Molecule? Systematic Review and Recommendations on the Use of Resveratrol," PLoS ONE 6(6):e19881, Jun. 2011, 11 pages.
Xue, M., et al., "Frequency Modulated Translocational Oscillations of Nrf2 Mediate the Antioxidant Response Element Cytoprotective Transcriptional Response," Antioxidants & Redox Signaling 23(7):613-629, 2015.
Xue, M., et al., "Transcriptional Control of Glyoxalase 1 by Nrf2 Provides a Stress-Responsive Defence Against Dicarbonyl Glycation," Biochemical Journal 443(1):213-222, Apr. 2012.
Yamamoto, T., et al., "Physiological Significance of Reactive Cysteine Residues of Keap1 in Determining Nrf2 Activity," Molecular and Cellular Biology 28(8):2758-2770, Apr. 2008.
Takumi, H., et al., "Bioavailability of Orally Administered Water-Dispersible Hesperetin and its efect on peripheral vasodilatation in human subjects: implication of endothelial functions of plasma conjugated metabolites," The Royal Society of Chemistry, (3)389-398, Feb. 2012.
Yoshino, J., et al., "Resveratrol Supplementation Does Not Improve Metabolic Function in Nonobese Women with Normal Glucose Tolerance," Elsevier Inc., Cell Metabolism 16, 658-664, Nov. 7, 2012.
Kanaze, F.I., et al., "Pharmacokinetics of the Citrus Flavanone Aglycones Hesperetin and Naringenin after Single Oral Administration in Human Subjects," European Journal of Clinical Nutrition, Nature Publishing Group, pp. 472-477, 2007.
Kanaze, F.I., et al., "Pharmacokinetics of the Citrus Flavanone Aglycones Hesperetin and Naringenin after Single Oral Administration in Human Subjects," European Journal of Clinical Nutrition, 61:472-477, 2007.
Boocock, D.J., et al., "Phase I Dose Escalation Pharmacokinetic Study in Healthy Volunteers of Resveratrol, a Potential Cancer Chemopreventive Agent," Cancer Epidemiol Biomarkers Prev 16(6):1246-1252, Jun. 2007.
Bresson, J.L., et al. (panel), "Safety of Synthetic Trans-Resveratrol as a Novel Food Pursuant to Regulation (EC) No 258/97 EFSA Panel on Dietetic Products, Nutrition and Allergies (NDA)" EFSA Journal 14(1):1-30, Jan. 2016.
Chen, M. et al., "Hesperidin Upregulates Heme Oxygenase-1 to Attenuate Hydrogen Peroxide-Induced Cell Damage in Hepatic L02 Cells," J. Agric. Food Chem. 58(6):3330-3335, Feb. 2010.
Silveira, J.Q., et al., "Pharmacokinetics of Flavanone Glycosides after Ingestion of Single Doses of Fresh-Squeezed Orange Juice versus Commercially Procesed Orange Juice in Healthy Humans," J. Agric. Food Chem. 62:12576-12584, 2014.
Shams-Rad, S., et al., "Hesperidin Supplementation has no Effect on Blood Glucose Control: A Systematic Review and Meta-Analysis of Randomized Controlled Clinical Trials," Br. J. Clin. Pharmacol. 86:13-22, 2020.

* cited by examiner

HESPERETIN AND TRANS-RESVERATROL COMPOSITIONS AND METHODS THEREOF

The invention relates to a composition, particularly for hair follicle growth.

Moi et al. (Proc. Natl. Acad. Sci. U.S.A, 91, 21, 9926-30 (October 1994)) discloses that nuclear factor erythroid-2 related factor 2 (also known as NFE2L2 or Nrf2) is a transcription factor (protein) that in humans is encoded by the NFE2L2 gene. According to Lee and Johnson (J. of Biochem. & Mol. Biol., 37, 139-143 (2004)) and Hybertson et al (Mol. Aspects Med., 32, 234-46 (2011)), Nrf2 has been shown to be involved in the defence against oxidative injury in various tissues. Under basal conditions, Nrf2 is inactive and bound in the cytoplasm by cytosolic regulatory protein Kelch-like erythroid cell-derived protein with CNC homology-associated protein 1 (Keap1). According to Cullinan et al. (Molec. Cell Biol., 24, 8477-8486 (2004)) the protein Cullin-3 degrades Nrf2 by ubiquitination. According to Kobayashi et al. (Mol. Cell. Biol., 24, 16, 7130-9 (August 2004)) Keap1 helps Cullin 3 ubiquitinate Nrf2. When Nrf2 is ubiquitinated, it is transported to the proteasome where it is degraded and its components recycled such that under normal conditions, according to Larance et al. (Molec. & Cellul. Proteomics, 12, 638-650 (2013)) Nrf2 has a half-life of about 5 hours.

Yamamoto et al. (Mol. Cell Biol., 28, 8, 2758-70 (April 2008)) and Sekhar et al. (Toxicol. Appl. Pharmacol., 244, 1, 21-6 (June 2009)) disclose that oxidative stress or electrophilic stress disrupts critical cysteine residues in Keap1, disrupting the Keap1-Cullin 3 ubiquitination system. When Nrf2 is not ubiquitinated, it builds up in the cytoplasm and translocates into the nucleus. Itoh et al. (Biochem. Biophys. Res. Commun., 236, 2, 313-22 (July 1997)) disclose that in the nucleus, Nrf2 combines (forms a heterodimer) with a small Maf protein (a transcription factor) and binds to small regions of DNA known as Antioxidant Response Elements (AREs) in the upstream promoter region of many antioxidative genes, and initiates their transcription.

According to Lee and Johnson and Hybertson et al., the antioxidant genes include "phase II" enzymes such as NAD(P)H: quinone oxidoreductase 1 (NQO-1) and hemoxygenase-1 (HO-1). Increased oxidative stress has been shown to have a detrimental effect on hair pigmentation (Lu et al., J Invest. Dermatol., 129, 1790-804 (2009); Arck et al., FASEB J., 2, 1567-9 (2006)).

The main function of the hair follicle is to produce a hair fibre. The hair follicle develops from the embryonic epidermis as an epidermal finger which differentiates into the fibre, the outer root sheath (ORS) and the inner root sheath (IRS). Mature follicles undergo follicular cycling through phases of organ growth and hair fibre production (anagen) for 3-7 years, cessation of fibre growth and organ involution (catagen) over about 2 weeks and a quiescent phase (telogen) which lasts about 3 months where the organ rests and the hair fibre remains anchored but no longer grows before the hair fibre falls (exogen) and is regenerated to start the cycle again (Dry, J. Genet., 16, 281-340 (1926), Chase, Physiol. Rev., 34, 1, 113-26 (1954) and Kligman, J. Invest. Dermatol., 33, 307-16 (1959)). WO 2014/095289 (Unilever et al.) discloses in Example 4 that sulforaphane significantly up-regulates NQO-1 and HO-1 gene expression in human hair follicles and is thus an Nrf2 agonist, and in Example 3 that sulforaphane significantly up-regulates human hair follicle growth.

Hair ageing is a major age-related consumer issue (hair loss, thinning hair, loss of shine, increased number of grey hairs, etc.). Biological routes for hair growth or preventing hair greying provide effective opportunities to target consumer hair issues. Currently, Minoxidil™ and Finasteride™ are the only clinically proven, mildly effective products available for hair growth and both are classified as medicines and therefore not suitable for cosmetic use. The identification of cosmetic ingredients that are able to boost hair growth, maintain anagen and/or prevent catagen may prove to be effective anti-ageing treatments to prevent or attenuate some of the symptoms associated with hair ageing.

According to Rabbani et al., (Biochem. Biophys. Res. Commun. 458, 221-226 (2015)) Methylglyoxal (MG) is a reactive, dicarbonyl metabolite formed mainly by the non-enzymatic degradation of triosephosphate intermediates of glucose metabolism—a minor "leak" of ca. 0.1% glucose flux. It is a highly potent modifying agent of protein and DNA. Although formed at relatively low flux, the high reactivity of MG leads to formation of some of the most quantitatively important endogenous damaging modifications of protein and DNA: arginine-derived hydroimidazolone MG-H1 and imidazopurinones MGdG. These are major protein and nucleotide advanced glycation endproducts (AGEs). The extent of protein and DNA modification by MG is usually low, 1-2% of protein and 1 in $10^5$ nucleotides, maintained at low tolerable levels by enzymatic detoxification of MG, mainly by Glo1 of the cytosolic glyoxalase system. The glyoxalase system consists of two enzymes: Glo1 and glyoxalase 2 (Glo2) and a catalytic amount of reduced glutathione (GSH). The major function of these enzymes is detoxification of MG to D-lactate. The detoxification process consists of two sequential reactions: Glo1 catalyses the conversion of MG and GSH to S-D-lactoylglutathione; and Glo2 catalyses the hydrolysis of S-D-lactoylglutathione to D-lactate, reforming GSH consumed in the Glo1-catalysed step. Glo1 directly controls the detoxification of MG. It is expressed in all mammalian cells and tissues.

Dicarbonyl stress is the presence of increased concentrations of MG and related dicarbonyl metabolites causing increased modification of protein and DNA leading to functional impairment and mutagenesis. It is a common characteristic of aging, diabetes and renal failure, and increasingly common in the human population in Westernised societies of increased median age and consuming a high carbohydrate, energy-rich diet. It is sustained by both increased flux of formation of MG in periods of glycolytic excess and decreases Glo1 activity through decreased expression and/or degradation. In recent studies dicarbonyl stress has emerged as a potential driver of insulin resistance, inflammation and weight gain in obesity and vascular cell dysfunction and dyslipidemia in cardiovascular disease. MG-modified proteins are inactivated and degraded such that increased MG modification decreases functional protein concentration and impairs cell phenotype, switching to insulin resistance, inflammation and extracellular matrix detachment. According to Thornalley et al., (Biochem. J. 375, 581-592 (2003)), degradation of MG-modified proteins releases MG-H1 free adduct from tissues which is excreted in urine.

According to Xue et al., (Biochem J 443, 213-222 (2012)), an effective strategy to counter dicarbonyl stress in susceptible cells and tissues is increase of Glo1 expression. Thereby in Glo1 overexpressing transgenic mice decline in metabolic health on a high fat diet and vascular disease in diabetes was prevented. Xue et al. found that a functional antioxidant response element (ARE) in the promoter of human GLO1 has expression up-regulated by activators of transcriptional factor Nrf2. According to Malhotra et al., (Nucleic Acids Research 38, 5718-5734 (2010)) Nrf2 controls basal and inducible expression of ca. 1,500 genes with typically a protective function. Nrf2 activators influence expression of ARE-linked gene subsets through differential recruitment of accessory proteins to the ARE-Nrf2 functional complex and differential response to increase in nuclear concentration of functionally active Nrf2. Recent advances in Nrf2 systems regulation have shown that Nrf2 undergoes constitutive translocational oscillations, increasing in frequency and mediating stimulation of transactivational activity, with multiple regulatory features—including acetylation and phosphorylation together with the conventional stimulation mechanism driven by disruption of complex Nrf2 with Keap1 and other members of the Nrf2 interactome (Xue et al., (2015) Antioxidants & Redox Signalling 23, 613-629). This indicates that a high efficacy response for induction of Glo1 expression could be achieved by a synergistic combination of Nrf2 activators inducers addressing different regulatory features of the Nrf2 system.

SUMMARY OF THE INVENTION

This invention is based on the observation that the combination of hesperetin (a flavanone, derivable from a natural rutinoside hesperetin 7-rutinoside (also known as hesperidin) in *citrus*, e.g., in *Citrus aurantium* L., *Citrus sinensis*, *Zanthozylum gilletti*, leaves of *Agathosma serratifolia*) and trans-resveratrol synergistically up-regulates HO-1 and NQO-1 in a gene expression assay.

It has also been observed that the combination of hesperetin and trans-resveratrol synergistically up-regulates ARE transcription in HepG2 cells stably transfected with glyoxalase 1 antioxidant response element (GLO1-ARE) or NQO-1—antioxidant response element (NQO-1—ARE) luciferase reporter gene machinery.

The stilbenoids, pterostilbene and piceatannol have also been observed to up-regulate ARE transcription in HepG2 cells stably transfected with glyoxalase 1 antioxidant response element (GLO1-ARE) or NQO-1—antioxidant response element (NQO-1—ARE) luciferase reporter gene machinery.

The flavanone eriodictyol has also been observed to up-regulate ARE transcription in HepG2 cells stably transfected with NQO-1—antioxidant response element (NQO-1—ARE) luciferase reporter gene machinery.

A randomised, placebo-controlled crossover clinical trial of trans-resveratrol and hesperetin co-formulation in overweight and obese subjects for 8 weeks has also shown induction of Glo1, decreased MG and MG-protein glycation. Treatment produced a decrease of insulin resistance, decreased fasting plasma glucose, modest weight loss and improvement in renal function, decreased vascular inflammation marker sICAM-1 and a trend of improvement in arterial dilatation and decreased risk of cardiovascular disease.

Thus in a first aspect of the invention, a composition is provided, the composition comprising a combination of:

(a) 30-10000, preferably 60-5000, most preferably 60-2500 mg in the form of an equivalent daily dose of flavanone of structure I:

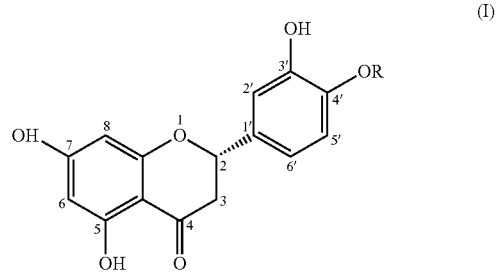

wherein R is —H or —CH3, and mono-, di- and tri-acylated derivatives of structure I; and (b) 20-1000, preferably 45-750, most preferably 45-500 mg in the form of an equivalent daily dose stilbenoid, wherein the composition comprises at least 0.5% w/w flavanone of structure I.

For the avoidance of doubt, on the phenyl ring the OR group is positioned on the para carbon (position 4') and the OH group is positioned on the meta carbon (position 3'). The flavanone may be the (S)-stereoisomer or the (R)-stereoisomer or a mixture of both.

By "equivalent daily dose" is meant that the composition need not only be administered daily but can also be administered at any regular rate, for example every other day or weekly, provided the equivalent daily dose, for example the weekly dose divided by 7, falls within the ranges set forth hereinabove. The composition may therefore comprise any multiple of the amount of flavanone of structure I specified in (a) and/or any multiple of the amount of the stilbenoid specified in (b). The composition may comprise any whole number multiple of the amount of flavanone of structure I specified in (a) and/or any whole number multiple of the amount of the stilbenoid specified in (b), such as twice, three times, four times, five times, six times, seven times, ten times, twenty times or thirty times the specified amount.

By the term "administration through the oral cavity" is included, but not exclusively sublingual administration.

By the term "administration by injection or infusion" is included, but not exclusively intravenous, intraperitoneal, intramuscular, subcutaneous and transdermal administration.

In a second aspect of the invention, the composition according to the first aspect of the invention is provided, for use in promoting hair follicle growth.

DETAILED DESCRIPTION OF THE INVENTION

In a first aspect, the invention relates to a composition, the composition comprising a combination of:

(a) 30-10000, preferably 60-5000, most preferably 60-2500 mg in the form of an equivalent daily dose of flavanone of structure I:

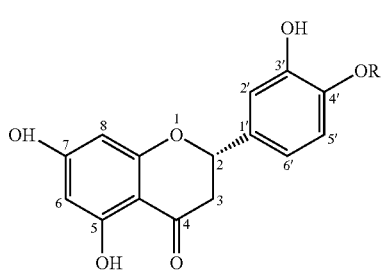

wherein R is —H or —CH3, and mono-, di- and tri-acylated derivatives thereof; and
(b) 20-1000, preferably 45-750, most preferably 45-500 mg in the form of an equivalent daily dose stilbenoid,
wherein the composition comprises at least 0.5% w/w flavanone of structure I.

The combination of the flavanone of structure I and the stilbenoid provides a synergistic effect, as shown in the examples.

Preferably the composition comprises at least 40 mg in the form of an equivalent daily dose of flavanone of structure I, more preferably at least 50, more preferably still at least 60, even more preferably at least 70, yet more preferably at least 80, yet more preferably still at least 100 mg in the form of an equivalent daily dose of flavanone of structure I.

Preferably the composition comprises at most 9000 mg in the form of an equivalent daily dose of flavanone of structure I, more preferably still at most 7500, even more preferably at most 5000, yet more preferably still at most 1000, yet more preferably at most 500, more preferably at most 400, more preferably still at most 300, even more preferably still at most 250 mg in the form of an equivalent daily dose of flavanone of structure I.

Preferably the composition comprises at least 25 mg in the form of an equivalent daily dose stilbenoid, more preferably at least 35, more preferably still at least 40, yet more preferably at least 45, even more preferably still at least 50, yet more preferably still at least 75 mg in the form of an equivalent daily dose stilbenoid.

Preferably the composition comprises at most 900 mg in the form of an equivalent daily dose stilbenoid, more preferably at most 750, more preferably still at most 600, even more preferably at most 500, yet more preferably still at most 400, even more preferably still at most 300, more preferably again at most 200, most preferably at most 150 mg in the form of an equivalent daily dose stilbenoid.

The composition of the invention may comprise 0.5 to 50, preferably 0.5 to 40, more preferably 0.5 to 30% w/w flavanone of structure I.

The composition of the invention may comprise 0.1 to 50, preferably 0.3 to 40, more preferably 0.3 to 30% w/w stilbenoid.

Preferably the weight ratio of flavanone according to formula 1 to the stilbenoid is from 5:1 to 1:5, preferably from 5:1 to 1:1.

Preferably the flavanone of structure I is selected from the group consisting of hesperetin (2,3-Dihydro-5,7-dihydroxy-2-(3-hydroxy-4-methoxyphenyl)-4H-1-benzopyran-4-one), eriodictyol (2-(3,4-Dihydroxyphenyl)-5,7-dihydroxy-4-chromanone) and mixtures thereof, more preferably the flavanone is hesperetin.

Preferably the stilbenoid is selected from the group consisting of trans-resveratrol, pterostilbene, piceatannol, and mixtures thereof.

More generally, the composition of the invention may be a foodstuff selected from the group consisting of a beverage, a supplement, a soup, margarine, a ready-to-eat meal, a dressing, a mayonnaise, mustard, a tomato-based condiment, a sauce, a seasoning, yoghurt and a frozen confection. Thus the composition of the invention may be in the form of a solid, a slurry, a solution, a suspension, a gel or an emulsion. More specifically, the composition of the invention may be in the form of a beverage, in particular a fruit or tea based beverage. Alternatively, the composition of the invention may be in the form of a supplement of one or more unit dosages such as capsules, sachets, lozenges, pills, tablets, caplets. The composition of the invention may also be a soup in dry, paste or liquid form, or a seasoning in unit doses in the form of a powder, a compressed powder in the form of, for example, a cube, a liquid or suspension, or a gel.

The composition is desirably suitable for promoting hair follicle growth.

In the invention, the composition may be adapted for administration in a variety of forms. Thus, it can be adapted for administration orally, for example as tablets, troches, lozenges, aqueous or oily suspensions, dispersible powders or granules. It may also be adapted for administration by enteral or parenteral routes such as via buccal, anal, pulmonary, intravenous, intra-arterial, intramuscular, intraperitoneal, intraarticular, topical or other appropriate administration routes The formulation of the composition will depend upon factors such as the nature of the exact components, etc. The composition typically comprises a pharmaceutically acceptable carrier or diluent. The pharmaceutical carrier or diluent may be, for example, an isotonic solution. For example, solid oral forms may contain, together with the active substance, diluents, e.g. lactose, dextrose, saccharose, cellulose, corn starch or potato starch; lubricants, e.g. silica, talc, stearic acid, magnesium or calcium stearate, and/or polyethylene glycols; binding agents; e.g. starches, gum arabic, gelatin, methylcellulose, carboxymethylcellulose or polyvinyl pyrrolidone; disaggregating agents, e.g. starch, alginic acid, alginates or sodium starch glycolate; effervescing mixtures; dyestuffs; sweeteners; wetting agents, such as lecithin, polysorbates, laurylsulphates; and, in general, non-toxic and pharmacologically inactive substances used in pharmaceutical formulations. Such pharmaceutical preparations may be manufactured in known manner, for example, by means of mixing, granulating, tabletting, sugar-coating, or film-coating processes.

Liquid dispersions for oral administration may be syrups, emulsions or suspensions. The syrups may contain as carriers, for example, saccharose or saccharose with glycerine and/or mannitol and/or sorbitol.

Suspensions and emulsions may contain as carrier, for example a natural gum, agar, sodium alginate, pectin, methylcellulose, carboxymethylcellulose, or polyvinyl alcohol. The suspensions or solutions for intramuscular injections may contain, together with the active substance, a pharmaceutically acceptable carrier, e.g. sterile water, olive oil, ethyl oleate, glycols, e.g. propylene glycol, and if desired, a suitable amount of lidocaine hydrochloride.

Solutions for intravenous administration or infusion may contain as carrier, for example, sterile water or preferably they may be in the form of sterile, aqueous, isotonic saline solutions.

For suppositories, traditional binders and carriers may include, for example, polyalkylene glycols or triglycerides;

such suppositories may be formed from mixtures containing the active ingredient in the range of 0.5% to 10%, preferably 1% to 2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and contain 10% to 95% of active ingredient, preferably 25% to 70%. Where the composition is lyophilised, the lyophilised material may be reconstituted prior to administration, e.g. a suspension. Reconstitution is preferably effected in buffer.

Capsules, tablets and pills for oral administration to an individual may be provided with an enteric coating comprising, for example, Eudragit "S", Eudragit "L", cellulose acetate, cellulose acetate phthalate or hydroxypropylmethyl cellulose.

Preferably the composition is adapted for administration through the oral cavity or by injection or infusion.

In a second aspect of the invention, the composition according to the first aspect of the invention is provided, for use in promoting hair follicle growth.

In a third aspect of the invention, the invention provides a method for promoting hair follicle growth in a patient, comprising administering the composition according to the first aspect of the invention to the patient. The composition may be administered in any of the ways discussed above with reference to the first aspect of the invention. Any patient may be treated in accordance with the invention. The patient is typically human. However, patient may be another mammalian animal, such as a commercially farmed animal, such as a horse, a cow, a sheep, a fish, a chicken or a pig, a laboratory animal, such as a mouse or a rat, or a pet, such as a guinea pig, a hamster, a rabbit, a cat or a dog. In addition to patients, the composition may also be administered to other animal, preferably human subject who are in a healthy or pre-disease state who would nevertheless benefit from the administration of the composition according to the first aspect of the invention.

In a fourth aspect of the invention, the composition according to the first aspect of the invention is provided, for use in treating or preventing a metabolic or vascular disease, inflammatory disease, neurological disease or cancer. The disease is preferably a metabolic or vascular disease. The metabolic or vascular disease is preferably diabetes (including vascular and other complications, nephropathy, retinopathy, neuropathy and cataract), obesity (such as related complications, particularly non-alcoholic fatty liver disease), insulin resistance, a cardiovascular disease or renal disease. The cardiovascular disease is preferably a coronary artery disease (CAD), such as angina or myocardial infarction, stroke, hypertensive heart disease, rheumatic heart disease, cardiomyopathy, atrial fibrillation, congenital heart disease, endocarditis, aortic aneurysms or peripheral artery disease. The vascular disease is preferably peripheral arterial disease (PAD).

In a fifth aspect of the invention, the invention provides a method for treating or preventing a metabolic or vascular disease, inflammatory disease (such as osteoarthritis, rheumatoid arthritis (RA) and other non-RA inflammatory disease), neurological disease (such as schizophrenia, Parkinson's disease and dementia), or cancer in a patient, comprising administering the composition according to the first aspect of the invention to the patient. The disease may be any of those discussed above with reference to the fourth aspect of the invention. The composition may be administered in any of the ways discussed above. The patient may be any of those discussed above with reference to the third aspect of the invention. The patient may be symptomatic. The patient may be asymptomatic. The patient may be suspected of having or developing the disease. The patient is preferably overweight or obese.

Treatment with the composition of the invention typically ameliorates one or more symptoms of the disease in the patient. Treatment with the composition of the invention preferably abolishes one or more of, or preferably all of, the symptoms of the disease in the patient. Prevention with the composition of the invention typically prevents one or more of, or preferably all of, the symptoms of the disease from developing in the patient. The composition preferably decreases the risk of a patient, such as an overweight or obese patient, developing type 2 diabetes and/or a cardiovascular disease.

The composition preferably decreases insulin resistance in the patient, particularly in highly overweight or obese patients (BMI>27.5 kg/m2). Insulin resistance can be measured using the Oral Glucose Insulin Sensitivity (OGIS) Index. The composition preferably decreases fasting plasma glucose in the patient. The composition preferably leads to weight loss in the patient. The composition preferably improves renal function in the patient. The composition preferably increases vascular function in the patient. This can be measured using brachial artery flow-mediated dilatation (FMD). The composition preferably results in arterial dilatation in the patient. The composition preferably decreases vascular inflammation markers, such as soluble intercellular adhesion molecule-1 (sICAM-1), in the patient. The composition preferably reduces the risk of cardiovascular disease in the patient. The composition preferably increases the activity of Glo1 in the patient's peripheral blood mononuclear cells (PBMCs). The composition preferably decreases the expression of hypoxia-inducible factor 1α (HIF1A), interleukin-8 (IL8) and prostaglandin endoperoxidase synthase-2 (PTGS2 or COX-2) in the patient's PMBCs. The composition preferably decreases the expression of CCL2, ferritin (FTH1), HIF1A, IL8, PTGS2 and RAGE in the patient's PBMCs, particularly in overweight or obese patients. The composition preferably decreases the expression of CCL2, HIF1A, IL8, KEAP1, PTGS2 and TNFα in the patient's PBMCs, particularly in obese patients.

Example 1

Gene Expression by Digital mRNA Profiling: Combination of Trans-Resveratrol and Hesperetin Human dermal foreskin BJ fibroblasts at cumulative population doubling of 22 were purchased from the European Collection of Animal Cell Cultures (Porton Down, UK). They were cultured in Eagle's Minimum Essential Medium (MEM) with 10% fetal calf serum and 2 mM glutamine under an atmosphere of 5% $CO_2$ in air, 100% humidity and 37° C.

Cells were seeded on 6-well plates in MCDB-131 medium with supplements (Life Technologies, UK) and cultured overnight at 37° C. under 5% $CO_2$ in air. Cells were treated with test compounds or vehicle (≤0.01% DMSO) for 12 hours after which cells were washed twice with ice-cold phosphate buffered saline (PBS) and total RNA was extracted using RNeasy Mini Kit (Qiagen). Total RNA (600 to 800 ng) was analyzed for mRNA copy number of target genes by the NanoString nCounter Gene Expression method described in Fortina et al. (Nature Biotechnology, 26, 293-

294 (2008)) (outsourced to Nanostring, Seattle, USA). A custom code set of genes including three reference genes (β-actin, clathrin heavy chain and β-glucuronidase) was designed.

Results

Results are presented in Table 1 which summarise levels of HO-1 and NQO-1 mRNA (counts as a % of vehicle control) in treated human dermal foreskin BJ fibroblasts, from which it is clear that combining 5 µM of each of hesperetin and trans-resveratrol in combination led to a synergistic increase in the levels of both HO-1 and NQO-1 mRNA.

TABLE 1

HO-1 and NQO-1 mRNA (relative mRNA copy numbers as a % of vehicle control) in treated human dermal foreskin BJ fibroblasts (n = 3). Errors calculated as standard deviations.

| | HO-1 mRNA (relative mRNA copy numbers as a % of vehicle control) | NQO-1 mRNA (relative mRNA copy numbers as a % of vehicle control) |
|---|---|---|
| 5 µM hesperetin | 95.4 ± 3.7 | 93.0 ± 3.5 |
| 5 µM trans-resveratrol | 115.3 ± 6.5 | 104.4 ± 1.2 |
| 5 µM hesperetin and 5 µM trans-resveratrol | 142.4 ± 5.0 | 132.4 ± 4.1 |

Conclusions

HO-1 and/or NQO-1 protein synthesis is synergistically up-regulated in human dermal foreskin BJ fibroblasts on treatment with a combination of 5 µM of each of hesperetin and trans-resveratrol. From reference to a combination of Examples 1 to 4 WO 2014/095289 (Unilever et al.), which shows in Examples 1, 2 and 4 that sulforaphane is an Nrf2 agonist in skin keratinocyte, dermal fibroblast and hair follicle cell assays, and in Example 3, that sulforaphane significantly up-regulates human hair follicle growth, it is clear that up-regulation of Nrf2 leads to up-regulation of human hair follicle growth. Therefore the results suggest, by analogy, that treatment of hair follicles with a combination of hesperetin and trans-resveratrol will result in up-regulation of their growth.

Example 2

Stable Transfectant GLO1-ARE Luciferase Reporter Cell Line: Combination of Trans-Resveratrol and Hesperetin A pGL4.22[luc2CP/puro] reporter vector containing GLO1-ARE was transfected into the HepG2 cell line according to the method set forth in Xue et al. (Biochem. J., 443, 213-222 (2012)). Transfected HepG2 cells were selected with puromycin (1 µg/ml). After culture for 3 weeks, puromycin-resistant cells were screened for luciferase activity after treatment with 4 µM sulforaphane for 6 hours. After validation of positive clones by measuring luciferase activity, the GLO1-ARE stable cell line, R1F3, was expanded in selection media.

Stable transfectant cell line R1F3 was incubated with and without test compounds for 6 hours in MEM with 10% fetal calf serum and 2 mM glutamine under an atmosphere of 5% $CO_2$ in air, 100% humidity and 37° C. For the reporter assay, 100 µl Cell Culture Lysis Reagent (CCLR, Promega) was added to cell and shaken gently for 30 minutes. The mixture of cell lysate was centrifuged (12,000 g, 5 minutes, 4° C.) and an aliquot (20 µl) of supernatant used in the reporter assay. The luciferase activity was determined using a Luciferase Assay System (Promega). The luciferase response is given in Relative Light Units (RLU).

Results

Results are presented in Table 2 which summarise levels of ARE transcription in HepG2 cells stably transfected with glyoxalase 1 antioxidant response element (GLO1-ARE) luciferase reporter gene machinery after treatment with from 0 to 10 µM trans-resveratrol or a combination of 5 µM hesperetin with from 0 to 10 µM trans-resveratrol. Data is corrected for blank response and normalised to positive control (blank=0%, 10 µM trans-resveratrol=100%).

TABLE 2

GLO1-ARE transcription in HepG2 cells stably transfected with glyoxalase 1 antioxidant response element (GLO1-ARE) luciferase reporter gene machinery after treatment with from 0 to 10 µM trans-resveratrol or a combination of 5 µM hesperetin with from 0 to 10 µM trans-resveratrol. Data corrected for blank response and normalised to positive control (blank = 0%, 10 µM trans-resveratrol = 100%) (n = 3). Errors are standard deviations.

| Trans-resveratrol (µM) | 0 µM hesperetin | 5 µM hesperetin |
|---|---|---|
| 0 | 0.0 ± 0.0 | 13.0 ± 1.6 |
| 0.625 | 4.0 ± 2.2 | 31.1 ± 3.7 |
| 1.25 | 19.2 ± 7.6 | 48.7 ± 4.3 |
| 2.5 | 53.8 ± 7.4 | 68.3 ± 0.3 |
| 5 | 67.6 ± 14.5 | 75.8 ± 8.8 |
| 10 | 100.0 ± 2.9 | 90.2 ± 1.8 |

It is clear that combining trans-resveratrol over a range of concentrations with 5 µM of hesperetin led to a synergistic increase in the levels of GLO1-ARE transcription in HepG2 cells. At trans-resveratrol concentrations of 5 and 10 µM, a synergistic effect on GLO1-ARE transcription in HepG2 cells in the presence of 5 µM of hesperetin was no longer observed. This is characteristic of synergistic competitive agonists.

Conclusions

Combinations of trans-resveratrol and hesperetin have been observed to provide a synergistic increase in the levels of ARE transcription in HepG2 cells, and hence synergistic activation of Nrf2 transactivational activity. Therefore in view of the relationship between the up-regulation of Nrf2 and hair follicle growth, it is expected that treatment of hair follicles with a combination of hesperetin and trans-resveratrol will result in up-regulation of their growth.

Example 3

NQO-1—ARE Luciferase Reporter Cell Line: Combination of Trans-Resveratrol and Hesperetin A pGL4.22[luc2CP/puro] reporter vector containing NQO-1-ARE was transfected into the HepG2 cell line according to the method set forth in Xue et al (Biochem J 443: 213-222, (2012)). Transfected HepG2 cells were selected with puromycin (1 µg/ml). After culture for 3 weeks, puromycin-resistant cells were screened for luciferase activity after treatment with 4 µM sulforaphane for 6 hours. After validation of positive clones by measuring luciferase activity, the NQO-1-ARE stable cell line was expanded in selection media.

Stable transfectant cell line was incubated with and without test compounds for 6 hours in MEM with 10% fetal calf serum and 2 mM glutamine under an atmosphere of 5% $CO_2$ in air, 100% humidity and 37° C. For the reporter assay, 100 µl Cell Culture Lysis Reagent (CCLR, Promega) was added to cell and shaken gently for 30 minutes. The mixture of cell lysate was centrifuged (12,000 g, 5 minutes, 4° C.) and an aliquot (20 µl) of supernatant used in the reporter assay. The luciferase activity was determined using a Luciferase Assay System (Promega). The luciferase response is given in Relative Light Units (RLU).

Results

Results are presented in Table 3 which summarise levels of ARE transcription in HepG2 cells stably transfected with NQO-1 antioxidant response element (NQO-1—ARE) luciferase reporter gene machinery after treatment with from 0 to 10 µM trans-resveratrol or a combination of 5 µM hesperetin with from 0 to 10 µM trans-resveratrol.

TABLE 3

NQO-1 - ARE transcription in HepG2 cells stably transfected with NQO-1 antioxidant response element (NQO-1 - ARE) luciferase reporter gene machinery after treatment with from 0 to 10 µM trans-resveratrol or a combination of 5 µM hesperetin with from 0 to 10 µM trans-resveratrol. Data corrected for blank response and normalised to positive control (blank = 0%, 10 µM trans-resveratrol = 100%) (n = 3). Errors are standard deviations.

| Trans-resveratrol (µM) | 0 µM hesperetin | 5 µM hesperetin |
| --- | --- | --- |
| 0 | 0.0 ± 0.0 | 7.9 ± 0.7 |
| 0.625 | 1.9 ± 8.6 | 9.5 ± 1.3 |
| 1.25 | 6.4 ± 2.5 | 21.7 ± 0.7 |
| 2.5 | 15.7 ± 6.7 | 48.3 ± 0.5 |
| 5 | 58.0 ± 2.5 | 70.6 ± 1.6 |
| 10 | 100.0 ± 10.0 | 100.0 ± 4.3 |

It is clear that combining trans-resveratrol over a range of concentrations with 5 µM of hesperetin led to a synergistic increase in the levels of NQO-1—ARE transcription in HepG2 cells. At trans-resveratrol concentrations of 1.25, 2.5 and 5 µM, a synergistic effect on NQO-1—ARE transcription in HepG2 cells in the presence of 5 µM of hesperetin was observed.

Conclusions

Combinations of trans-resveratrol and hesperetin have been observed to provide a synergistic increase in the levels of ARE transcription in HepG2 cells, and hence synergistic activation of Nrf2 transactivational activity. Therefore in view of the relationship between the up-regulation of Nrf2 and hair follicle growth, it is expected that treatment of hair follicles with a combination of hesperetin and trans-resveratrol will result in up-regulation of their growth.

Example 4

Stable Transfectant GLO1-ARE Luciferase Reporter Cell Line: Other Stilbenoids

The assay described in Example 2 was employed to determine whether stilbenoids other than resveratrol were Nrf2 agonists.

Results

Results are presented in Table 4 which summarise levels of ARE transcription in HepG2 cells stably transfected with glyoxalase 1 antioxidant response element (GLO1-ARE) luciferase reporter gene machinery after treatment with 5 µM pterostilbene and piceatannol, as compared to the same concentration of trans-resveratrol. Data is corrected for blank response and normalised to positive control (blank=0%, 10 µM trans-resveratrol=100%).

TABLE 4

ARE transcription in HepG2 cells stably transfected with glyoxalase 1 antioxidant response element (GLO1-ARE) luciferase reporter gene machinery after treatment with 5 µM pterostilbene and piceatannol, as compared to the same concentration of trans-resveratrol. Data corrected for blank response and normalised to positive control (blank = 0%, 10 µM trans-resveratrol = 100%) (n = 3). Errors calculated at standard deviations.

| Stilbenoid (5 µM) | |
| --- | --- |
| Trans-resveratrol | 67.6 ± 14.5 |
| Pterostilbene | 37.5 ± 18.3 |
| Piceatannol | 61.3 ± 31.0 |

It is clear that pterostilbene and piceatannol up-regulate GLO1-ARE transcription in HepG2 cells and hence are Nrf2 agonists.

Conclusions

Pterostilbene and piceatannol are, together with trans-resveratrol, Nrf2 agonists.

Example 5

NQO-1—ARE Luciferase Reporter Cell Line: Other Stilbenoids and Flavanones

The assay described in Example 3 was employed to determine whether stilbenoids other than resveratrol, and flavanones, other than hesperetin (also known as eriodictyol 4'-methyl ether), were Nrf2 agonists.

Results

Results are presented in Table 5 which summarise levels of ARE transcription in HepG2 cells stably transfected with NQO-1 antioxidant response element (NQO-1—ARE) luciferase reporter gene machinery after treatment with 5 µM of the stilbenoids pterostilbene, piceatannol and the flavanones eriodictyol and naringenin, as compared to the same concentration of trans-resveratrol. Data is corrected for blank response and normalised to positive control (blank=0%, 10 µM trans-resveratrol=100%).

TABLE 5

ARE transcription in HepG2 cells stably transfected with NQO-1 antioxidant response element (NQO-1 - ARE) luciferase reporter gene machinery after treatment with 5 µM pterostilbene, piceatannol, eriodictyol and naringenin, as compared to the same concentration of trans-resveratrol. Data corrected for blank response and normalised to positive control (blank = 0%, 10 µM trans-resveratrol = 100%) (n = 3). Errors calculated at standard deviations.

| Stilbenoid or flavanone (5 µM) | |
| --- | --- |
| Trans-resveratrol | 56.9 ± 1.7 |
| Pterostilbene | 41.8 ± 2.7 |
| Piceatannol | 66.6 ± 2.4 |
| Eriodictyol | 95.3 ± 14.7 |
| Naringenin | -2.75 ± 5.24 |

It is clear that pterostilbene, piceatannol and eriodictyol up-regulate NQO-1—ARE transcription in HepG2 cells and hence are Nrf2 agonists. However, naringenin does not up-regulate NQO-1—ARE transcription in HepG2 cells and hence is not an Nrf2 agonist.

Conclusions

Pterostilbene, piceatannol and eriodictyol are, together with trans-resveratrol, Nrf2 agonists. Naringenin is not an Nrf2 agonist.

Example 6

To identify Glo1 inducers and characterise pharmacological synergism in the response we employed a functional activity, luciferase reporter-based screen based on the GLO1-ARE. To minimise the risk of toxicity and facilitate clinical translation, we focused on dietary bioactive compounds occurring at trace levels in dietary food stuffs of differing classes with established Nrf2 activator activity: isothiocyanates, flavonoids, stilbenoids, triterpenoids, polyphenols, carotenoids and others.

Bioactive Screening for Glo1 Inducers

We developed stable transfectant luciferase reporter cell lines with transcription regulatory elements: GLO1-ARE (ARE-1 from our previous notation), mutated functionally inactive GLO1-ARE (␣RE1m, negative control) and quinone reductase (NQO1)-ARE—a conventional ARE-related marker gene. Screening criteria were: increased transcriptional response in the concentration range 0.625-5.0 µM and without significant cytotoxicity to human endothelial cells and fibroblasts in primary culture at the highest concentration. We screened 95 compounds and identified 9 inducers of GLO1-ARE of 4 different structural classes of dietary bioactive and 24 inducers of NQO1-ARE of 8 different structural classes under these section conditions. The bioactive compound giving the highest GLO1-ARE transcriptional response in screening assays was trans-resveratrol (tRES) which was also positive in the NQO1-ARE transcriptional assay. The bioactive compound giving the lowest median effective concentration $EC_{50}$ for GLO1-ARE transcriptional activity was hesperetin (HESP). Further examination and refinement of the responses gave the following GLO1-ARE response characteristics: tRES, $EC_{50}$=2.52±0.19 µM, logistic regression coefficient n=3.92±0.39 µM and $E_{max}$ 100.0±8.9%; and HESP, $EC_{50}$=0.59±0.01 µM, logistic regression coefficient n=2.01±0.02 and $E_{max}$ 24.4±0.1%. A dietary supplement of 150 mg HESP achieved a peak plasma concentration of 6.7 µM HESP (Takumi et al., Food & Function 3, 389-398 (2012)), suggesting that HESP may be a competent and effective Glo1 inducer for clinical translation. A dietary supplement of 500 mg tRES achieved a peak plasma concentration of ca. 0.3 µM (Boocock et al., Cancer Epidemiology Biomarkers & Prevention 16, 1246-1252 (2007)) or 10-fold lower than the $EC_{50}$ for the GLO1-ARE response. To enhance pharmacological efficacy we studied the pharmacological synergism of tRES and HESP together. Study of the GLO1-ARE transcriptional response of 5 µM HESP with 0.625-10 µM tRES showed that HESP combined synergistically with tRES, decreasing the $EC_{50}$ of tRES to 1.46±0.10 µM whilst maintaining the $E_{max}$. The predicted increase of GLO1-ARE transcriptional response of 0.1-1.0 µM tRES in the presence of 5 µM HESP was 3-79 fold, including up to 79% increased GLO1-ARE transcriptional response over additive effects, suggesting there is expected to be marked pharmacological benefit of a tRES-HESP co-formulation through pharmacological additive and synergistic effects.

Safety assessments of tRES and HESP indicate that they are highly tolerated—as reviewed in Vang et al., PLoS ONE 6, e19881 (2011) and Parhiz et al., Phytotherapy Research 29, 323-331 (2015). Cytotoxicity in human BJ fibroblasts in primary culture showed no toxicity of tRES and HESP individually or with 5 µM combination with primary bioactive compound at concentrations ≤20 µM. tRES (40 µM) with 5 µM HESP and HESP (40 µM) with and without 5 µM tRES showed minor decrease in viability of BJ cells in vitro. tRES (5 µM) with 0.625 µM HESP gave a minor increase in cell number—which may an effect on fibroblast growth of insulin sensitising activity of tRES-HESP in combination.

Validation of Glo1 Inducer Screening Results and Functional Effects

To validate the Glo1 inducer studies we measured the change in Glo1 mRNA and protein and functional responses—cellular concentration of MG and MG-modified protein—in human hepatocyte-like HepG2 cell line in vitro and human aortal endothelial cells (HAECs) and BJ fibroblasts in primary culture. There was a 10-30% increase in Glo1 mRNA in cells incubated with tRES and HESP and combined, and similar increases in Glo1 protein. We studied the effect of 5 µM tRES, 5 µM HESP and 5 µM tRES and HESP combined on protein markers of HAECs and BJ fibroblasts related to "cell vitality"—inflammatory response markers and extracellular matrix degradation. In HAECs, the treatments decreased cellular levels of intercellular adhesion molecule-1 (ICAM-1), the receptor for advanced glycation endproducts (RAGE) and E-selectin protein, with synergistic effect for decreases in ICAM-1 and RAGE. In BJ fibroblasts, the treatments decreased cellular vascular adhesion molecule-1 (VCAM-1), RAGE and matrix metalloproteinase-3 protein (MMP), with synergism for tRES and HESP in decrease of VCAM-1 and MMP-3; in the latter case, tRES decreases MMP-3 and prevents an increase of MMP3 induced by HESP alone. Activation of Nrf2 is often associated with increased cellular GSH and increased GSH/oxidised glutathione (GSSG) ratio through induction of expression of genes GSH synthesis and metabolism—particularly γ-glutamylcysteine ligase, modulatory subunit (GCLM) and catalytic subunits (GCLC), and glutathione reductase. Treatment of HAECs, BJ fibroblasts and HepG2 cells with 5 µM tRES and 5 µM HESP did not change cellular levels of GSH and GSSG whereas treatment with 5 µM tRES and HESP combined increased cellular GSH content by 43% in BJ fibroblasts and 32% in HepG2 cells. Cellular GSSG content was unchanged with 5 µM tRES and HESP in BJ fibroblasts and showed a minor increase (0.6% total GSH) in HepG2 cells.

We also studied time-dependent changes in expression of ARE-linked genes and other genes linked to metabolism and vitality in HAECs, BJ fibroblast and HepG2 cells induced by 5 µM tRES and HESP, individually and in combination, by focused quantitative mRNA. Overall, there were additive and synergistic changes of gene expression, and in some cases, synergism prevented an adverse effect of tRES of HESP treatment individually. For example, in HAECs, expression of the characteristic gene markers of Nrf2 activation, glutathione transferase A4 (GTSA4) and haem oxygenase-1 (HMOX-1), were increased, as where expressions of GCLM, GCLC and GSR—cellular mRNA often maximising at 12-24 h. tRES and HESP tended to increased ICAM1 mRNA individually at 48 h and 6 h post-treatment, respectively, whereas added together they decreased ICAM-1 mRNA only at 24 h. In BJ fibroblasts, tRES and HESP synergised to increase cellular mRNA of ARE-linked genes GSTP1, HMOX1, NQO1 and aldoketo reductase 1C1 (AKR1C1) and to decrease expression of inflammation markers CCL2 (gene of monocyte chemotactic protein-1 MCP-1) and ICAM-1. Finally, in HepG2 cells also tRES and HESP combined synergistically to increase expression of ARE-linked genes NQO1, GCLM and GLLC. There was, however, also synergistic increase in expression of low density lipoprotein receptor (LDLR) for increased hepatic catabolism of LDL, and increased inducible hexokinase-2 (HK2) and 6-phosphofructokinase/bisphosphatase-3 (PFKBP3) implicated in improved sensitivity to insulin. As tRES and HESP have known pharmacology and high clinical tolerability and safety—being compounds present in red grape juice and juice of oranges and related *citrus* fruits, respectively—we were able to attempt to translate our finding to clinical application.

Improvements in Metabolic and Vascular Health of Trans-Resveratrol-Hesperetin Co-Formulation in Overweight and Obese Subjects.

A tRES-HESP co-formulation (90 mg tRES and 120 mg HESP, once daily) was evaluated in healthy overweight and obese subjects in a double-blinded, randomised, placebo-controlled crossover study with treatment for 8 weeks and intervening washout period of 6 weeks—Healthy Ageing Through Functional Food (HATFF or Hats-off) study (NCT02095873, Clinicaltrials.gov). Primary clinical endpoints were: metabolic health—marker of insulin resistance in an oral glucose tolerance test (oGTT); and vascular health—brachial artery flow mediated dilatation (FMD). There were 29 participants: 20 highly overweight/obese (BMI>27.5 kg/m$^2$), and 11 obese (BMI>30 kg/m$^2$). We measured compliance and evidence of increased exposure to tRES and HESP during treatment by measurement of urinary excretion of metabolites over 24 h. In the placebo arm at baseline and post-supplementation and tRES-HESP treatment arm at baseline, urinary tRES metabolites were undetectable and HESP metabolites were low. Post-supplementation of the tRES-HESP treatment arm urinary excretion of tRES and HESP metabolites were increased markedly such that participants had median exposure to tRES and HESP had increased >2000-fold and >100 fold, respectively, during the tRES-HESP treatment.

tRES-HESP produced a 22% increase in Glo1 activity of peripheral blood mononuclear cells (PBMCs) post-treatment, compared to placebo in all subjects. This tended to increase with increasing BMI; PBMC Glo1 activity was increased 27% in highly overweight/obese and 30% in obese sub-groups. Consistent with this was a 37% decrease in plasma MG post-supplementation with tRES-HESP but not with placebo in highly overweight/obese subjects was found. There was no change in plasma D-lactate concentration—a surrogate indicator of flux of MG formation. This indicates that tRES-HESP-induced increase in Glo1 activity of PBMCs and expected similar increases in Glo1 expression and activity of Glo1 of other blood cells and tissues produced the decrease in plasma MG concentration but likely did not change the flux of MG formation.

To assess the effect of tRES-HESP against the primary metabolic endpoint, we used the Oral Glucose Insulin Sensitivity (OGIS) index to assess insulin resistance. OGIS is a surrogate indicator, correlating strongly to reference method glucose clamp studies (Mari et al., Diabetes Care 24, 539-548 (2001)). With tRES-HESP there was a positive correlation of change in OGIS from baseline ($\Delta$OGIS) with BMI; r=0.45, P<0.05. There was no similar correlation with placebo. In the subset of highly overweight and obese participants, there was an increase in OGIS post supplementation with tRES-HESP ($\Delta$OGIS=+42 mlmin$^{-1}$m$^{-2}$) but not with placebo. This effect was further enhanced in obese subjects only ($\Delta$OGIS=+58 mlmin$^{-1}$m$^{-2}$). The main contributory factors to this effect were: (i) a trend towards decreased plasma insulin during the oGTT; (ii) decreased fasting plasma glucose (FPG); and (iii) a trend towards decreased area under the curve plasma glucose (AUCg). The magnitude of $\Delta$OGIS, 42-58 mlmin$^{-1}$m$^{-2}$, is comparable to that achieved with drug treatment of patients with type 2 diabetes (for example, 1.7 g metformin per day, $\Delta$OGIS=+54 mlmin$^{-1}$m$^{-2}$)[13] and 6-months post-gastric band surgery in morbid obesity (23 kg weight loss, $\Delta$OGIS=+62 mlmin$^{-1}$m$^{-2}$)[14]. tRES-HESP treatment therefore would likely effectively counter insulin resistance in the highly overweight and obese population.

Improvements in insulin resistance were reflected in improved FPG and area under the curve plasma glucose (AUCg) in the oGTT with tRES-HESP. FPG in the total subject group was tending to decrease post-treatment with tRES-HESP compared to placebo (3.97 mM versus 3.83 mM, P=0.08). With tRES-HESP there was a negative correlation of change in FPG from baseline ($\Delta$FPG) to BMI; r=−0.41, P<0.05. There was no similar correlation with placebo. In the highly overweight and obese subjects, there was a significant decrease in FPG post supplementation with tRES-HESP but not with placebo. This effect was further enhanced in obese subjects only. tRES-HESP treatment therefore decreases FPG in the highly overweight and obese population. There was a suggestion of improvement in AUCg with tRES-HESP which just failed to reach significance in the highly overweight/obese study group. Concomitant with increased metabolic health there were small decreases in BMI and body weight in the obese subjects with tRES-HESP: −0.5 kg/m$^2$ and 0.3 kg, respectively. Other significant changes were a small, 3% increase in glomerular filtration rate (GFR) and an 11% decrease in plasma urea with tRES-HESP but not with placebo.

We assessed improvement in vascular function by brachial artery flow-mediated dilatation (FMD)—a measure of endothelium-dependent, nitric oxide (NO) vasodilatation, with glyceryl trinitrate (GTN) administration to assess endothelium-independent vasodilatation (GTND), and the FMD-to-GTND ratio to characterize NO dilator function in the context of smooth muscle cell sensitivity. We found no change in FMD and GTND. For GTND, normalising from baseline, in the highly overweight/obese subject group, $\Delta$FMD/$\Delta$GTND tended towards an increase with tRES-HESP. $\Delta$FMD/$\Delta$GTND (mean±SEM): placebo, −0.09±0.53, tRES-HESP, +1.12±0.47; P=0.08, paired t-test. The 95% confidence interval for $\Delta$FMD/$\Delta$GTND with tRES-HESP was 0.13-2.11. Mean $\Delta$GTND for the tRES-HESP treatment arm was 0.2 mm. Hence, $\Delta$FMD/$\Delta$GTND=+1.12 corresponds to a $\Delta$FMD of ca. 0.2 mm. Baseline artery diameter was 3.2±0.9 mm and hence tRES-HESP treatment approached a significant change of ca. 7% of arterial diameter.

Markers of vascular inflammation were assessed. There was a highly significant decrease in change of sICAM1 from baseline with tRES-HESP in all subjects (mean±SEM): placebo, +25.8±6.4 versus tRES-HESP, −3.6±6.9 ng/ml; P<0.01 (−10% from post-supplementation) for placebo. This was driven mainly by increased sICAM1 from baseline in the placebo arm. Vascular inflammation markers unchanged by tRES-HESP treatment were sVCAM-1, CRP and sE-E-selectin.

Glo1 inducers were designed and developed to decrease MG concentration in tissues and body fluids and thereby prevent protein glycation. To assess the effect on protein glycation in the HATFF study we analysed glycation—and also oxidation and nitration—adduct residue content of plasma protein. Plasma protein content of MG-H1 residues was unchanged with tRES-HESP treatment but the content of oxidative crosslink dityrosine (DT) residues was decreased 21% with tRES-HESP treatment but not by placebo. To assess the whole body formation of MG-H1 we measured the urinary excretion of MG-H1 free adduct—measured in second void urine after overnight fast to decrease the contribution of glycation adducts from food. Glycation adducts from food are still present, however—as evidenced by the presence of the glycation adduct pyrraline formed at high temperatures of culinary processing and hence originating almost exclusively from digested proteins in food (Foerster et al., Biochem. Soc. Trans. 31, 1383-1385 (2003)). Pyrraline is metabolised little post-absorption and therefore urinary provides a biochemical measure of food consumption, assuming little change in diet composition and thermal processing. There was no change in urinary pyrraline excretion of subjects with placebo or tRES-HESP, suggesting food consumption was similar throughout the study (which was supported by food questionnaires). Total urinary excretion of MG-H1 free adduct was not changed significantly with tRES-HESP treatment but it correlated positively with urinary pyrraline for all 4 study visits (r=0.43-0.63, P=0.019-<0.001). MG-H1 is formed endogenously by glycation of proteins by MG and is also absorbed from food protein after digestion of MG-modified proteins in food. Linear regression of urinary MG-H1 free adduct excretion on urinary pyrraline excretion and extrapolation to zero pyrraline excretion gave a non-zero intercept which is an estimate of the flux of MG-H1 formed endogenously. The flux of endogenously-generated MG-H1 adducts was ca. 13 nmol/24 h at baseline and decreased by 14% with tRES-HESP treatment but not with placebo. The pentose-derived crosslink, pentosidine, is a quantitatively minor and fluorescence AGE. It is marker of pentosephosphate pathway activity and correlates with insulin resistance in experimental models. Pentosidine in dietary protein has poor bioavailability and so urinary pentosidine free adduct is sourced endogenously. Consistent with this, urinary pentosidine did not correlate with urinary pyrraline excretion. Urinary excretion of pentosidine free adduct was decreased 32% by treatment with tRES-HESP by not by placebo.

We also analysed changes in gene expression of PBMCs in a focused quantitative mRNA array study. In all subjects there was evidence of increased expression of GLO1 and decreased expression of hypoxia-inducible factor 1α (HIF1A), interleukin-8 (IL8) and prostaglandin endoperoxidase synthase-2 (PTGS2 or COX-2). In highly overweight/obese subjects there was decreased expression of CCL2, ferritin (FTH1), HIF1A, IL8, PTGS2 and RAGE; and in obese subjects decreased CCL2, HIF1A, IL8, KEAP1, PTGS2 and TNFα.

We assessed clinical safety of the tRES-HESP formulation by study of a comprehensive range of clinical chemistry and haematological markers. The levels of these markers were normal at study entry and remained unchanged throughout the placebo and tRES-HESP treatment periods.

Methods and Materials

Tissue culture materials, medium MCDB-131, L-glutamine and recombinant human epidermal growth factor were from Invitrogen (Paisley, UK) and fetal bovine serum from Biosera (Ringmer, UK). Human Glo1 antibody was available from a previous preparation as set out in Allen et al., J. Prot. Chem. 12, 111-119 (1993). Dietary bioactive compounds were purchased from Extrasynthese (69727 Genay Cedex, France), LKT Laboratories Inc. (St. Paul, Minn. 55130, USA) and Sigma (Poole, UK). [$^2$H$_3$]HESP was from Toronto Research Chemicals (Toronto, Canada). Antibodies used were: anti-VCAM1 (ab174279), anti-CD62E (ab137732), anti-CD62P (ab178424), anti-RAGE (ab172473), anti-MMP3 (ab137659) purchased from Abcam (Cambridge, UK). Other chemicals used were from Sigma.

NQO1-ARE and GLO-ARE and Stable Transfectant Reporter Cells Lines.

These were produced by transfection of a pGL4.22 [luc2CP/puro] reporter vector containing NQO1-ARE or GLO1-ARE into the HepG2 cell line. Transfected HepG2 cells were selected with puromycin (1 μg/ml). After culture for 3 weeks, puromycin-resistant cells were screened for luciferase activity after treatment with 4 μM SFN for 6 h. After validation of positive clones by measuring luciferase activity, the stable cell line was expanded in selection media and thereafter used in studies for screening of bioactive compounds and synergism. Stable transfectant cell lines were incubated with and without bioactive compounds and combination of tRES and HESP (0.625-5.0 μM) for 6 h in MEM medium with 10% fetal calf serum and 2 mM glutamine under an atmosphere of 5% CO2 in air, 100% humidity and 37° C. This incubation period was optimum to judge initial rate of increase in transcriptional response in cells treated with compounds without increase in untreated controls. For the reporter assay, 100 μl Cell Culture Lysis Reagent (CCLR, Promega, Southampton, UK) was added to cell and shaken gently for 30 min. The mixture of cell lysate was centrifuged (12,000 g, 5 min, 4° C.) and an aliquot (20 μl) of supernatant used in the reporter assay. The luciferase activity was determined using a Luciferase Assay System (Promega). The luciferase response is given in Relative Light Units (RLU). Data are corrected for blank response and normalised to the highest effect (100%) achieved with 10 μM tRES. Data of normalised responses (blank=0%, 10 μM tRES=100%) for varied bioactive concentrations are fitted by non-linear regression to a dose-response curve, $E=E_{max} \times [\text{Bioactive}]^n/(EC_{50}^n+[\text{Bioactive}]^n)$, solving for $EC_{50}$ and n (logistic regression coefficient—also called the Hill coefficient). Nrf2-dependent transcriptional response was verified by siRNA silencing of Nrf2, as described in Xue et al., Biochem J 443, 213-222 (2012).

Primary Human Cell Culture.

Primary human aortal endothelial cells (HAEC) were purchased from Lonza (Slough, U.K). HAEC cells were grown in proprietary large vessel endothelial cell basal media supplemented with large vessel endothelial cell growth supplement (containing hydrocortisone, human epidermal growth factor, human fibroblast growth factor with heparin and in 2% (/v/) FBS), 25 μg/ml gentamicin and 50 ng/ml amphotericin B. Human dermal foreskin BJ fibroblasts at cumulative population doubling of 22 were purchased from the European Collection of Animal Cell Cultures (Porton Down, UK). They were cultured in MEM medium with 10% fetal calf serum and 2 mM glutamine under an atmosphere of 5% $CO_2$ in air, 100% humidity and 37° C.

ARE-Linked Gene and Other Cell Metabolism and Vitality Marker Gene Expression by Digital mRNA Profiling.

HAECs, BJ fibroblasts and HepG2 cells, (5×10$^5$ cells/well) were seeded on 6-well plates in MCDB-131 medium and cultured overnight at 37° C. under 5% $CO_2$/air. Cells were treated with and without 5 μM tRES, 5 μM tHESP and 5 μM tRES & HESP combined or vehicle (0.002% DMSO) and cultured further for up to 48 h. At desired time point, cells were washed twice with ice-cold PBS and total RNA was extracted using RNeasy Mini Kit (Qiagen). Total RNA (600-800 ng) was analysed for mRNA copy number of target genes by the NanoString nCounter Gene Expression method[45] (outsourced to Nanostring, Seattle, USA). Custom codeset of genes including three reference genes (β-actin, clathrin heavy chain and β-glucuronidase) was designed. Similar studies were performed with PBMC RNA extracts from the HATFF study.

Immunoblotting for Glo1 and Functional Markers.

This was performed as described in Xue et al., Biochem J 443, 213-222 (2012). Protein extracts (30 μg) were subjected to SDS-PAGE on 10% polyacrylamide gels. After electrophoresis, the proteins were transferred electrophoretically to PVDF membrane and the membrane blocked with 5% non-fat milk in Tris-buffered saline with Tween-20 (TBST) buffer (10 mM Tris-HCl, pH 7.5, 150 mM NaCl, 0.05% Tween-20) and probed with rabbit anti-human Glo1 antibody. The membrane was incubated at 4° C. overnight. After washing, the membrane was incubated with horseradish peroxidase conjugate second antibody for 1 h at room temperature. Immunoreactivity was detected with enhanced chemiluminescence (ECL) and intensities of protein bands were quantified by software ImageQuant TL (GE Healthcare). For reference protein, β-actin, the membrane was stripped with stripping buffer (100 mM 3-mercaptoethanol, 2% SDS, 62.5 mM Tris-HCl pH 6.8), blocked with 5% non-fat milk in TBST buffer and re-probed with anti-1-actin antibody with ECL detection.

Clinical HATFF Study.

Healthy human subjects, overweight and obese were recruited at the University Hospitals Coventry & Warwickshire (UHCW) NHS Trust, Coventry, U.K. in the period May-July 2014 and the last participant left the study in December 2014. All of the participants gave written, informed consent. Main inclusion criteria were: age 18-80 years, BMI 25-40 kg/m$^2$, with normal, impaired fasting or impaired postprandial glucose. The main exclusion criteria were: severe hypertriglyceridemia, uncontrolled hypertension, CVD, relevant renal or hepatic disease, diabetes, and other relevant morbidity; severe excess alcohol consumption (>14/21 units/week for women/men), smoking, under pharmacological treatment affecting glucose and lipid metabolism or blood coagulation, or taking herbal remedies, known food allergies, women who are pregnant or breast feeding. At a pre-screening visit assessment where made for meeting the inclusion criteria and failing the exclusion criteria in which the following clinical chemistry was performed: 2 h plasma glucose in an oGTT and A1C, ALT, AST, plasma triglycerides, plasma creatinine (for GFR estimation). The HATFF study was of randomized, double-blind, placebo-controlled crossover design of 32 subjects. All subjects were evenly randomised in intervention and placebo arms (n=16) by the Clinical Trials Unit at University of Warwick. Dietary supplementation was given in hard gelatin capsules (Conisnap size 0) containing: active—90 mg tRES-120 mg HESP, 108.4 mg mannitol and 1.6 mg silica; and placebo—108.4 mg mannitol, 1.6 mg silica and maize starch in place of bioactives. Capsules were taken once daily for 8 weeks, followed by 6 weeks washout and then switch to the alternative capsule for 8 weeks. Dietary advice in both intervention arms was given to maintain the usual diet, confirmed by dietary questionnaires at the start and end of the treatment periods. There participants filed to complete the study and study data are analysed per protocol (n=29). The primary clinical endpoints were: (i) effect on metabolic health assessed by oGTT and calculation of insulin sensitivity by OGIS (from plasma glucose concentrations at 0, 90 and 120 min and plasma insulin concentrations at 0 and 90 min) (Parhiz et al., Phytotherapy Research 29, 323-331 (2015)); and (ii) brachial artery FMD (Black et al., Am J Physiol Heart Circ Physiol 297, H1109-H1116 (2009)).

A standard 75 g glucose oGTT will be performed. Participants were instructed to eat carbohydrate rich diet (>150 g/day) for at least three days before the test, followed by an overnight fast. During the oGTT 5 mL of venous blood was obtained at 0, 15, 30, 60, 90 and 120 min post glucose load using a venous cannula. Vascular function measurements were performed between 8 am and 10 am in a quiet temperature-controlled room maintained at 23±1° C. Brachial blood pressure was recorded in both arms using a validated oscillometric technique (Omron Corporation). Both readings were taken in duplicate or triplicate and the arm with the higher blood pressure was used for measuring vascular studies. Same arm was used for the study at all 4 visits for comparative study results. Arterial function was determined by recording the diameter changes in the brachial artery in response to increased blood flow generated during reactive hyperaemia (FMD) and GTN (GTND). The brachial artery was identified using high-resolution vascular ultrasound (Terason 3200T Portable Ultrasound Monitor with a 7- to 10-MHz linear array transducer) and images collected real-time and processed in QUIPU FMD STUDIO Ultrasound Suite software (Smart Medical, Moreton-in-Marsh, U.K.). A B-mode image of the artery was scanned in longitudinal section 5 to 10 cm above the antecubital fossa. Once an optimal image of the vessel wall was obtained, the probe was fixed in place using a stereotactic clamp. The image was then updated from the R-wave of the ECG. End-diastolic images of the vessel were then acquired every 3 seconds using the acquisition software throughout the study and were stored offline for later analysis. Images were recorded for 1 min before a pressure cuff, around the forearm, distal to the elbow, inflated above suprasystolic pressure for 5 min. After deflation of the cuff, the change in vessel diameter (endothelial-dependent dilatation) was measured for a further 5 min. Seven minutes after cuff deflation, a second baseline scan was recorded for 1 min. A 25 µg dose of GTN was then administered sublingually, and the arterial dilatation (endothelial-independent dilatation) was measured over a period of 5 min. Maximum arterial dilatation in FMD and GTND (mm) were recorded. Measurements were conducted in a quiet, temperature-controlled room after 5 min of seated rest. Subjects were asked to attend fasting after having omitted any morning medication.

Venous blood samples were drawn at weeks 0, 8, 14, and 22 (50 ml) in the fasting state prior to the oGTT. Blood cells were sedimented by centrifugation (2000 g, 10 min), buffy coat removed and PBMCs isolated by Ficol-Hypaque density gradient centrifugation, and plasma snap frozen and stored at −80° C. until analysis. The following measurements were made: plasma: glucose (fasting), ALT, AST, total cholesterol, HDL cholesterol, LDL+VLDL cholesterol, triglycerides, cystatin c, plasma creatinine, sVCAM-1, C-reactive protein (CRP), endothelin-1, insulin, sE-selectin, sICAM-1, MG, and markers of plasma protein damage by glycation, oxidation and nitration ($N_\varepsilon$-fructosyl-lysine FL, $N_\varepsilon$-carboxymethyl-lysine CML, MG-H1, $N_\varepsilon$-carboxymethyl-arginine CMA, pentosidine, glucosepane, methionine sulfoxide MetSO, dityrosine DT, 3-nitrotyrosine 3-NT, glutamic semialdehyde GSA, α-aminoadipic semialdehyde AASA); red blood cells—A1C and haemoglobin; peripheral blood mononuclear cells—activity of Glo1 and NQO1, focussed mRNA array (Nanostring method); and urine—creatinine hesperetin, resveratrol and metabolites, markers of protein damage—glycated oxidised and nitrated amino acids (FL, CML, MG-H1, CMA, pentosidine, glucosepane, MetSO, DT, 3-NT, GSA, AASA).

Safety assessment of tRES-HESP co-formulation was assessed by ECG and analysis of blood markers: plasma aspartate aminotransferase, alanine aminotransferase, γ-glutamyl transferase and alkaline phosphatase activities, plasma concentrations of albumin, total protein, bilirubin sodium, potassium, chloride, phosphate and urea, whole blood haemoglobin, red blood cells count, mean corpuscular volume, leukocyte count, thrombocyte number and prothrombin clotting time.

For power calculation we judged decrease in AUCg of the oGTT would be 10%; cf. 30% decreased achieved with a high purified cereal fibre intake (30 g per day) in a short-term study. With a 30% dropout, 32 subjects were required for significance α=0.05 and power (1-β)=0.80.

The study was approved by National Research Ethics Service (NRES) Committee West Midlands—Coventry & Warwickshire (project number 13/WM/0368) and registered on the Clinicaltrials.gov (identifier: NCT02095873). The procedures followed were in accordance with institutional guidelines and the Declaration of Helsinki.

Assay of Total Urinary Metabolites of tRES and HESP.

Total tRES and HESP urinary metabolites were determined by stable isotopic dilution analysis liquid chromatography tandem mass spectrometry (LC-MS/MS) after de-conjugation of glucuronides and sulphates. An aliquot of urine (20 µl), from which cells had been sedimented and removed prior to storage, was treated with 50 mM ammonium acetate buffer, pH 4.9 (50 µl), water (10 µl) and a solution of internal standards (250 µM [$^{13}$C$_6$]tRES and 10 µM d$_4$-HESP; 20 µl) and incubated for 2 h at 37° C. in the dark with 1-glucuronidase (5 µl, 17,000 U/ml; from *Helix pomatia*, Sigma cat no. G0876) and 1-sulphatase (5 µl, 1,000 U/ml; from *Helix pomatia*, Sigma cat no. S9626). This de-conjugation method was validated with authentic glucuronides and sulphates of rRES and HESP before use. Thereafter ice-cold methanol (100 µl) was added for de-proteinisation and samples vortex mixed, centrifuged (10,000 g, 10 min, 4° C.), filtered (0.2 µm pore size) and analysed by LC-MS/MS. tRES, cis-RES, HESP and related stable isotopic standards were detected by positive ion multiple reaction monitoring LC-MS/MS. Analyte retention time $R_t$, molecular ion mass, fragment ion mass, cone voltage and collision energy for detection were: tRES—$R_t$=5.0 min, 229.2 Da, 134.8 Da, 36 V and 18 eV; cis-RES— as for tRES except $R_t$=7.2 min; [$^{13}$C$_6$]tRES–$R_t$=5.0 min, 235.2 Da, 134.8 Da, 36 V and 18 eV; HESP–$R_t$=10.0 min, 303.2 Da, 152.9 Da, 34 V and 27 eV; and [$^2$H$_3$]HESP–$R_t$=10.0 min, 306.2 Da, 152.9 Da, 34 V and 27 eV. The capillary voltage was 3.7 kV, extractor voltage 4 V, electrospray source temperature 120° C. and desolvation gas 350° C. The desolvation and cone nitrogen gas flows were 750 L/h and 200 L/h, respectively. Calibration curves were constructed by analysis of 125-625 pmol tRES and HESP. The limit of detection (3×SD of the zero analyte control on regression of analyte/internal standard peak area ratio on analyte in the calibration curve) in urine was: tRES, 2 nM, and HESP—10 nM. The chromatography column was BEH C18, 1.7 µm particle size 100×2.1 mm column fitted with a 5×2.1 mm pre-column at 30° C. (Waters, UK). The sample temperature was maintained at 4° C. in the autosampler. The mobile phases were: A, 25% acetonitrile (MeCN) and 0.1% trifluoroacetic acid (TFA) in water; B, 0.1% TFA in MeCN; and C, 50% tetrahydrofuran in 0.1% TFA. The flow rate was 0.2 ml/min. Samples runs started with 100% A and a linear gradient of 0-37.5% B over 10 min and isocratic 27.5% B from 10-15 min. The column is then washed for 20 min with 100% solvent C and re-equilibrated for 10 min with 100% solvent A. The column temperature was 30° C. Analyses was performed with a Acquity-Quattro Premier XE LC-MS/MS system (Waters, Manchester, U.K.). No cis-RES was detected, indicating no detectable geometric isomerisation of administered tRES, and no eriodctyol (demethylated HESP), was detected in study samples.

The invention claimed is:

1. A composition comprising a combination of:
   (a) 120 mq to 500 mg of hesperetin; and
   (b) 90 mg to 900 mg of trans-resveratrol,
   wherein the composition comprises at least 0.5% w/w hesperetin.

2. The composition according to claim 1, wherein the composition comprises 0.5 to 50% w/w hesperetin.

3. The composition according to claim 1, wherein the composition comprises 0.1 to 50% w/w trans-resveratrol.

4. The composition according to claim 1, wherein the weight ratio of hesperetin to trans-resveratrol is from 5:1 to 1:5.

5. The composition according to claim 1, wherein the composition is adapted for administration through the oral cavity or by injection or infusion.

6. The composition according to claim 1, wherein the composition comprises 90 mq to 750 mg of trans-resveratrol.

7. The composition according to claim 1, wherein the composition comprises 90 mq to 500 mg of trans-resveratrol.

8. The composition according to claim 1, wherein the composition comprises 0.5 to 40% w/w hesperetin.

9. The composition according to claim 1, wherein the composition comprises 0.5 to 30% w/w hesperetin.

10. The composition according to claim 1, wherein the composition comprises 0.3 to 40% w/w trans-resveratrol.

11. The composition according to claim 1, wherein the composition comprises 0.3 to 30% w/w trans-resveratrol.

12. The composition according to claim 1, wherein the weight ratio of hesperetin to the trans-resveratrol is from 5:1 to 1:1.

13. The composition according to claim 1 wherein the composition comprises 120 mg of hesperetin.

* * * * *